(12) United States Patent
Fisher et al.

(10) Patent No.: US 7,100,606 B2
(45) Date of Patent: Sep. 5, 2006

(54) METHOD OF MAINTAINING CONSTANT ARTERIAL PCO₂ AND MEASUREMENT OF ANATOMIC AND ALVEOLAR DEAD SPACE

(76) Inventors: Joseph Fisher, 603 Clarke Avenue West, Unit 21, Thornhill, Ontario (CA) L4J 8P9; Alex Vesely, P.O. Box 622, Station "Q", Toronto, Ontario (CA) M4T 2N4; Hiroshi Sasano, 5785 Yonge Street, Suite 505, Toronto, Ontario (JP) M2M 4J2; Steve Iscoe, Department of Physiology, Botterell Hal, Room 439, Queen's University, Kingston, Ontario (CA) K7L 3N6; Ronald Somogyi, 46 Dallas Road, Toronto, Ontario (CA) M2R 2J6

( * ) Notice: Subject to any disclaimer, the term of this patent is extended or adjusted under 35 U.S.C. 154(b) by 0 days.

(21) Appl. No.: 10/838,481

(22) Filed: May 4, 2004

(65) Prior Publication Data

US 2004/0206354 A1    Oct. 21, 2004

Related U.S. Application Data

(63) Continuation of application No. 10/135,655, filed on Apr. 30, 2002, now Pat. No. 6,799,570, which is a continuation-in-part of application No. 09/676,899, filed on Oct. 2, 2000.

(30) Foreign Application Priority Data

May 4, 2001    (CA)    .................................... 2346517

(51) Int. Cl.
*A61M 16/00*    (2006.01)
(52) U.S. Cl. ........................... 128/204.18; 128/205.24; 128/203.12

(58) Field of Classification Search ........... 128/204.18, 128/204.21–204.23, 204.26, 204.28, 204.29, 128/205.11, 205.13–205.17, 205.24, 203.12, 128/205.18, 914
See application file for complete search history.

(56) References Cited

U.S. PATENT DOCUMENTS

| 3,901,230 | A | 8/1975 | Henkin |
| 4,188,946 | A | 2/1980 | Watson et al. |
| 4,991,576 | A | 2/1991 | Henkin et al. |
| 5,255,675 | A | 10/1993 | Kolobow |

(Continued)

FOREIGN PATENT DOCUMENTS

WO    WO 96/36385    11/1996

*Primary Examiner*—Henry Bennett
*Assistant Examiner*—Amadeus Lopez
(74) *Attorney, Agent, or Firm*—Stetina Brunda Garred & Brucker

(57) ABSTRACT

A method to maintain isocapnia for a subject. A fresh gas is provided to the subject when the subject breathes at a rate less than or equal to the fresh gas flowing to the subject. The fresh gas flow equal to a baseline minute ventilation minus a dead space gas ventilation of the subject contains a physiological insignificant amount of $CO_2$. An additional reserve gas is provided to the subject when the subject breathes at a rate more than the fresh gas flowing to the subject. The reserve gas has a partial pressure of carbon dioxide equal to an arterial partial pressure of carbon dioxide of the subject. A breathing circuit is applied to the method to maintain isocapnia for a subject. The breathing circuit has an exit port, a non-rebreathing valve, a source of fresh gas, a fresh gas reservoir and a reserve gas supply.

23 Claims, 7 Drawing Sheets

U.S. PATENT DOCUMENTS

| | | |
|---|---|---|
| 5,320,093 A | 6/1994 | Raemer |
| 5,398,675 A | 3/1995 | Henkin et al. |
| 5,497,767 A | 3/1996 | Olsson |
| 5,507,280 A | 4/1996 | Henkin et al. |
| 5,957,128 A | 9/1999 | Hecker et al. |
| 6,158,434 A | 12/2000 | Lugtigheid |
| 6,165,105 A | 12/2000 | Boutellier et al. |
| 6,227,196 B1 | 5/2001 | Jaffe et al. |
| 6,354,292 B1 | 3/2002 | Fisher |
| 6,612,308 B1 * | 9/2003 | Fisher et al. ........... 128/205.11 |
| 6,622,725 B1 | 9/2003 | Fisher et al. |
| 6,655,382 B1 | 12/2003 | Kolobow |

* cited by examiner

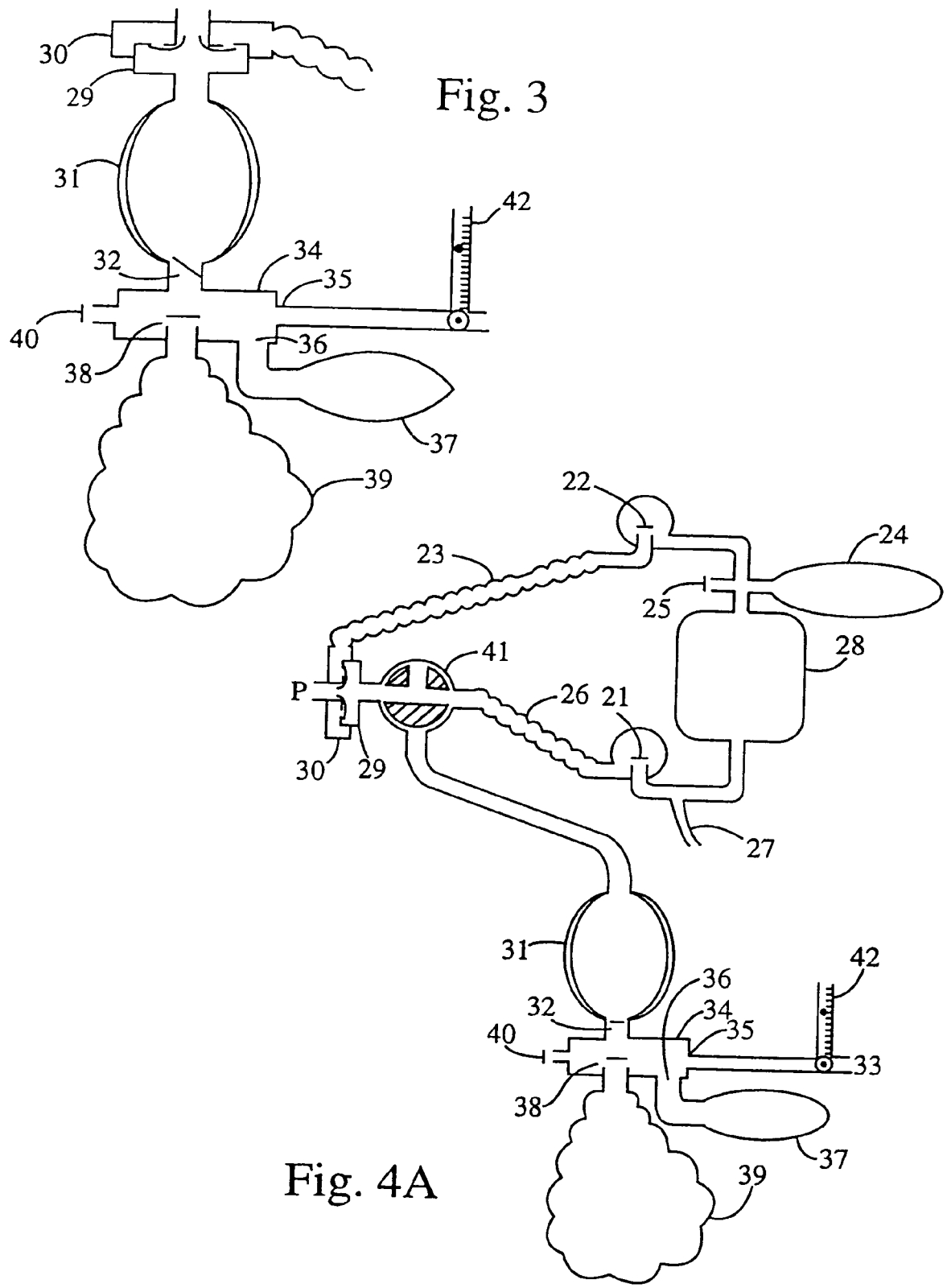

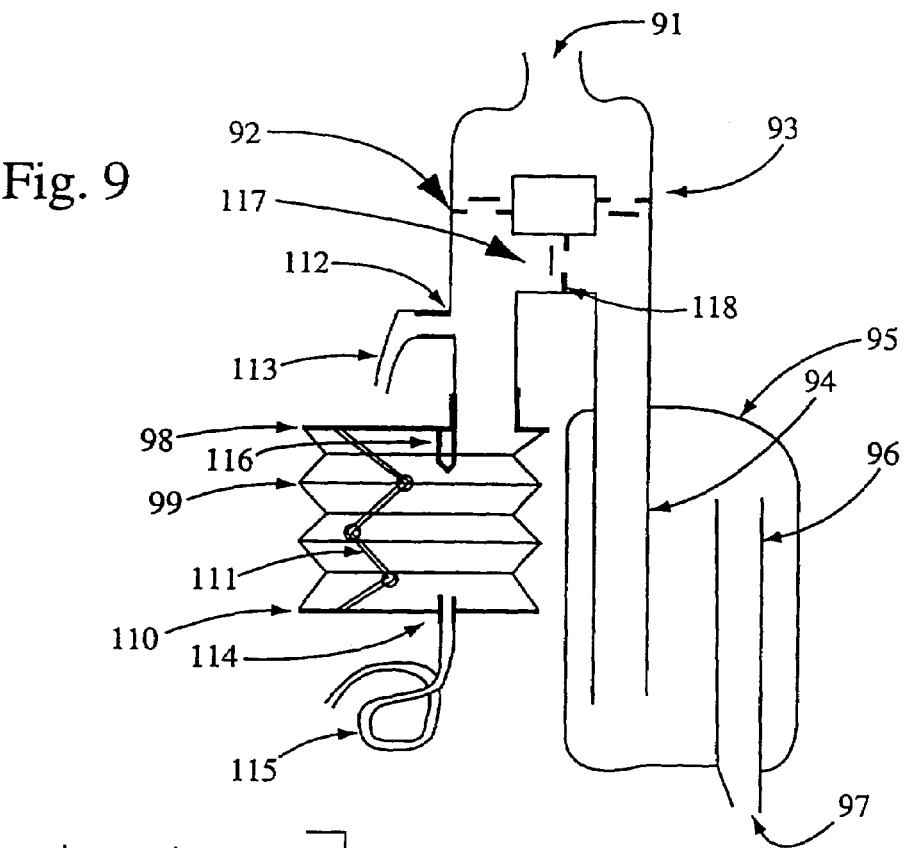
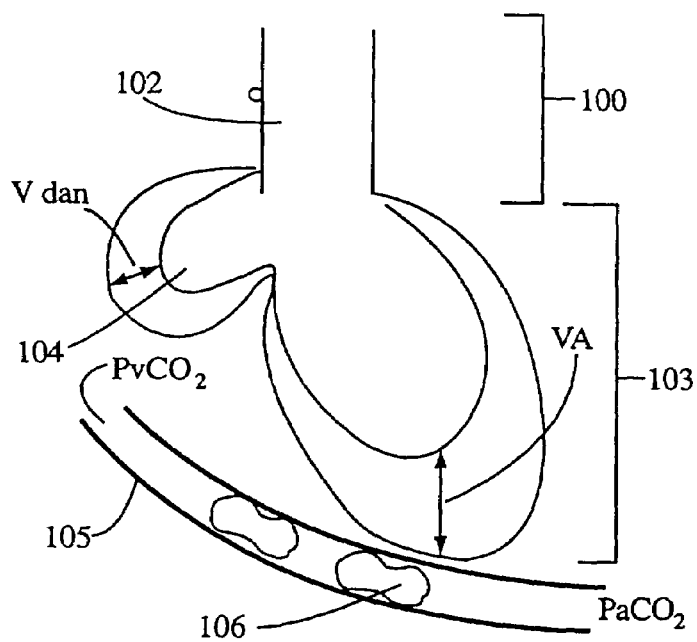
Fig. 9
Fig. 10

METHOD OF MAINTAINING CONSTANT ARTERIAL PCO$_2$ AND MEASUREMENT OF ANATOMIC AND ALVEOLAR DEAD SPACE

RELATED APPLICATIONS

The present application is a continuation of U.S. application Ser. No. 10/135,655 entitled "METHOD OF MAINTAINING CONSTANT ATERIAL PCO$_2$ AND MEASUREMENT OF ANATOMIC AND ALVEOLAR DEAD SPACE" filed Apr. 30, 2002, now U.S. Pat. No. 6,799,570 which is a continuation-in-part of application Ser. No. 09/676,899, filed on Oct. 2, 2000.

STATEMENT RE FEDERALLY SPONSORED RESEARCH/DEVELOPMENT (Not applicable)

BACKGROUND OF INVENTION

The present invention relates to a method to maintain isocapnia when breathing exceeds baseline breathing and a circuit therefor. Preferably, the circuit includes a non-rebreathing valve, a source of fresh gas, a fresh gas reservoir and a source of gas to be inhaled when minute ventilation exceeds fresh gas flow. Preferably the flow of the fresh gas is equal to minute ventilation minus anatomic dead space. Any additional inhaled gas exceeding fresh gas flow has a partial pressure of $CO_2$ equal to the partial pressure of $CO_2$ of arterial blood.

Venous blood returns to the heart from the muscles and organs partially depleted of oxygen ($O_2$) and a full complement of carbon dioxide ($CO_2$). Blood from various parts of the body is mixed in the heart (mixed venous blood) and pumped into the lungs via the pulmonary artery. In the lungs, the blood vessels break up into a net of small vessels surrounding tiny lung sacs (alveoli). The vessels surrounding the alveoli provide a large surface area for the exchange of gases by diffusion along their concentration gradients. After a breath of air is inhaled into the lungs, it dilutes the $CO_2$ that remains in the alveoli at the end of exhalation. A concentration gradient is then established between the partial pressure of $CO_2$ ($PCO_2$) in the mixed venous blood ($PvCO_2$) arriving at the alveoli and the alveolar $PCO_2$. The $CO_2$ diffuses into the alveoli from the mixed venous blood from the beginning of inspiration (at which time the concentration gradient for $CO_2$ is established) until an equilibrium is reached between the $PCO_2$ in blood from the pulmonary artery and the $PCO_2$ in the alveolae at some time during breath. The blood then returns to the heart via the pulmonary veins and is pumped into the arterial system by the left ventricle of the heart. The $PCO_2$ in the arterial blood, termed arterial $PCO_2$ ($PaCO_2$) is then the same as was in equilibrium with the alveoli. When the subject exhales, the end of his exhalation is considered to have come from the alveoli and thus reflects the equilibrium $CO_2$ concentration between the capillaries and the alveoli. The $PCO_2$ in this gas is the end-tidal $PCO_2$ ($P_{ET}CO_2$). The arterial blood also has a $PCO_2$ equal to the $PCO_2$ at equilibrium between the capillaries and alveoli.

With each exhaled breath some $CO_2$ is eliminated and with each inhalation, fresh air containing no $CO_2$ is inhaled and dilutes the residual equilibrated alveolar $PCO_2$, establishing a new gradient for $CO_2$ to diffuse out of the mixed venous blood into the alveoli. The rate of breathing, or ventilation ($V_E$), usually expressed in L/min, is exactly that required to eliminate the $CO_2$ brought to the lungs and establish an equilibrium $P_{ET}CO_2$ and $PaCO_2$ of approximately 40 mmHg (in normal humans). When one produces more $CO_2$ (e.g. as a result of fever or exercise), more $CO_2$ is carried to the lungs and one then has to breathe harder to wash out the extra $CO_2$ from the alveoli, and thus maintain the same equilibrium $PaCO_2$. But if the $CO_2$ production stays normal, and one hyperventilates, then excess $CO_2$ is washed out of the alveoli and the $PaCO_2$ falls.

It is important to note that not all $V_E$ contributes to elimination of $CO_2$. The explanation for this is with reference to the schematic in the lung depicted in FIG. 10. The lung contains two regions that do not participate in gas equilibration with the blood. The first comprises the set of conducting airways (trachea and bronchi) 100 that act as pipes directing the gas to gas exchanging areas. As these conducting airways do not participate in gas exchange they are termed anatomic dead space 102 and the portion of $V_E$ ventilating the anatomic dead space is termed anatomic dead space ventilation ($V_{Dan}$). The same volume of inhaled gas resides in the anatomic dead space on each breath. The first gas that is exhaled comes from the anatomic dead space and thus did not undergo gas exchange and therefore will have a gas composition similar to the inhaled gas. The second area where there is no equilibration with the blood comprises the set of alveoli 103 that have lost their blood supply; they are termed alveolar dead space 104. The portion of $V_E$ ventilating the alveolar dead space is termed alveolar dead space ventilation ($V_{Dalv}$). Gas is distributed to alveolar dead space in proportion to their number relative to that of normal alveoli (normal alveoli being those that have blood vessels and participate in gas exchange with blood). That portion of $V_E$ that goes to well perfused alveoli and participates in gas exchange is called the alveolar ventilation ($V_A$). In FIG. 10, the numeral references 105 and 106 indicate the pulmonary capillary and the red blood cell, respectively.

Prior art circuits used to prevent decrease in $PCO_2$ resulting from increased ventilation, by means of rebreathing of previously exhaled gas are described according to the location of the fresh gas inlet, reservoir and pressure relief valve with respect to the patient. They have been classified by Mapleson and are described in Dorsch and Dorsch pg 168.

Mapleson A

The circuit comprises a pressure relief valve nearest to the patient, a tubular reservoir and fresh inlet distal to the patient. In this circuit, on expiration, dead space gas is retained in the circuit, and after the reservoir becomes full, alveolar gas is lost through the relief valve. Dead space gas is therefore preferentially rebreathed. Dead space gas has a $PCO_2$ much less than $PaCO_2$. This is less effective in maintaining $PCO_2$ than rebreathing alveolar gas, as occurs with the circuit of the present invention.

Mapleson B and C

The circuit includes a relief valve nearest the patient, and a reservoir with a fresh gas inlet at the near patient port. As with Mapleson A dead space gas is preferentially rebreathed when minute ventilation exceeds fresh gas flow. In addition, if minute ventilation is temporarily less than fresh gas flow, fresh gas is lost from the circuit due to the proximity of the fresh gas inlet to the relief valve. Under these conditions, when ventilation once again increases, there is no compensation for transient decrease in ventilation as the loss of fresh gas will prevent a compensatory decrease in $PCO_2$.

Mapleson D and E

Mapleson D consists of a circuit where fresh gas flow enters near the patient port, and gas exits from a pressure relief valve separated from the patient port by a length of reservoir tubing. Mapleson E is similar except it has no pressure relief valve allowing the gas to simply exit from an opening in the reservoir tubing. In both circuits, fresh gas is lost without being first breathed. The volume of gas lost without being breathed at a given fresh flow is dependent on the pattern of breathing and the total minute ventilation. Thus the alveolar ventilation and the $PCO_2$ level are also dependent on the pattern of breathing and minute ventilation. Fresh gas is lost because during expiration, fresh gas mixes with expired gas and escapes with it from the exit port of the circuit. With the present invention, all of the fresh gas is breathed by the subject.

There are many different possible configurations of fresh gas inlet, relief valve, reservoir bag and $CO_2$ absorber (see Dorsch and Dorsch, pg. 205–207). In all configurations, a mixture of expired gases enters the reservoir bag, and therefore rebreathed gas consists of combined dead space gas and alveolar gas. This is less efficient in maintaining $PCO_2$ constant than rebreathing alveolar gas preferentially as occurs with our circuit, especially at small increments of V above the fresh gas flow.

BRIEF SUMMARY OF THE INVENTION

The present invention comprises a method and a circuit that maintains a constant $PCO_2$. More particularly, the present invention maintains a constant $PCO_2$ by:

1) setting FGF equal to the baseline minute ventilation less the anatomical dead space ventilation ($V_{Dan}$); and
2) establishing $PrgCO_2$ being equal to the $PaCO_2$ rather than the $PvCO_2$ to increase accuracy of the methods herein disclosed.

In the present invention, when minute ventilation is temporarily less than fresh gas flow, no fresh gas is lost from the circuit. Instead, the reservoir acts as a buffer to store extra fresh gas. When ventilation increases once more, the subject breathing the accumulated fresh gas allows $PCO_2$ to return to the previous level.

A circuit to maintain isocapnia is also provided by the invention. The circuit includes a non rebreathing valve, a source of fresh gas, a fresh gas reservoir and a source of gas to be inhaled when minute ventilation exceeds fresh gas flow. Preferably, the flow of fresh gas is equal to minute ventilation minus anatomic dead space. Any additional inhaled gas exceeding fresh gas flow has a partial pressure of $CO_2$ equal to the partial pressure of $CO_2$ of arterial blood.

The invention further provides a method of measuring anatomical and/or alveolar dead space ventilation by using a breathing circuit consisting of a non rebreathing valve, a source of fresh gas, a fresh gas reservoir and a source of gas with a partial pressure of $CO_2$ substantially equal to that of arterial blood.

In one embodiment of the invention, the non-rebreathing circuit comprises an exit port, a non-rebreathing valve, a source of fresh gas, a fresh gas reservoir, and a reservoir gas supply. From the exit port, gases are supplied from the circuit to the patient. The non-rebreathing valve has a one-way valve permitting gases to be delivered to the exit port to the patient, but prevents gases from passing into the circuit. The source of fresh gas may be oxygen, air or the like excluding $CO_2$ (air containing physiologically insignificant amount of $CO_2$) and is in communication with the non-rebreathing valve to be delivered to the patient. The fresh gas reservoir is in communication with the source of fresh gas flow for receiving excess fresh gas not breathed by the patient from the source of fresh gas and for storage thereof, wherein as the patient breathes gas from the source of fresh gas flow and from the fresh gas reservoir are available depending on the minute ventilation level. The reserve gas supply contains $CO_2$ and other gases (usually oxygen) preferably having a partial pressure of the $CO_2$ approximately equal to the partial pressure of $CO_2$ in the arterial blood of the patient. The reserve gas supply is delivered to the non-rebreathing valve to make up that amount of gas required by the patient for breathing that is not fulfilled from the gases delivered from the source of fresh gas flow and the fresh gas reservoir. The source of gas, the fresh gas reservoir and the reserve gas supply are disposed on the side of the non-breathing valve remote from the exit port.

Preferably, a pressure relief valve is provided in the circuit in communication with the fresh gas reservoir in the event that the fresh gas reservoir overfills with gas so that the fresh gas reservoir does not break, rupture or become damaged in any way.

The reserve gas supply preferably includes a demand valve regulator. When additional gas is required, the demand valve regulator opens the communication of the reserve gas supply to the non-rebreathing valve for delivery of the gas thereto. When additional gas is not required, the demand valve regulator is closed and only fresh gas flows from the source of fresh gas and from the fresh gas reservoir to the non-rebreathing valve. The source of fresh gas is set to supply fresh gas (non-$CO_2$-containing gas) at a rate equal to desired alveolar ventilation for the elimination of $CO_2$, that is, the baseline minute ventilation minus anatomical dead space.

The basic concept of the present invention is when breathing increases, flow of fresh gas (inspired $PCO_2$=0) from the fresh gas flow contributing to elimination of $CO_2$ is kept constant, and equal to the baseline minute ventilation minus anatomical dead space. The remainder of the gas inhaled by the subject (from the reserve gas supply) has a $PCO_2$ equal to that of arterial blood, resulting in the alveolar $PCO_2$ stabilizing at the arterial $PCO_2$ level regardless of the level of ventilation as long as minute ventilation minus anatomical dead space is greater than the fresh gas flow. In the event that the desired $PaCO_2$ is a particular value, which may be higher or lower than the initial $PaCO_2$ of the subject, then the $PCO_2$ having an adjustable feature of the reserve gas may simply be set equal to the desired $PaCO_2$. If the $PaCO_2$ is specifically desired to remain equal to the initial $PaCO_2$ of the subject, then the $PaCO_2$ can be measured by obtaining a sample of arterial blood from any artery, and the $PCO_2$ of the reserve gas set equal to this valve. Alternatively, an estimation of the $PaCO_2$ can be made from $P_{ET}CO_2$. $P_{ET}CO_2$ is determined by measuring the $PCO_2$ of expired breath using a capnograph usually present or easily available in medical and research facilities to persons skilled in the art.

In effect, the present invention passively causes the amount of $CO_2$ breathed in by the patient to be proportional to the amount of total breathing, thereby preventing any perturbation of the arterial $PCO_2$. This is unlike prior art servo-controllers which always attempt to compensate for changes. Persons skilled in the art, however, may choose to automate the circuit by using a servo-controller or computer to monitor minute ventilation levels and deliver inspired gas with the concentrations of $CO_2$ substantially equal to that of those from fresh gas and reserve gas were the gases mixed together.

The non-rebreathing circuit provided by the present invention can also be used to enable a patient to recover more quickly from, and to hasten the recovery of the patient after vapor anaesthetic administration, or poisoning with carbon monoxide, methanol, ethanol, or other volatile hydrocarbons.

According to another aspect of the invention, a method of treatment of an animal or person is provided. The method comprises delivering to a patient gases which do not contain $CO_2$ at a specific rate, and gases containing $CO_2$ to maintain the same $PCO_2$ in the patient, at the rate of ventilation of the patient which exceeds the rate of administration of the gases which do not contain $CO_2$ independent of the rate of ventilation.

The circuit and method of treatment can also be used for any circumstance where it is desirable to dissociate the minute ventilation from elimination of carbon dioxide such as respiratory muscle training, investigation of the role of pulmonary stretch receptors, tracheobronchial tone, expand the lung to prevent atelectasis, exercise, and control of respiration and other uses as would be understood by those skilled in the art.

The circuit and method of treatment of the present invention may also be used by deep sea divers and astronauts to eliminate nitrogen from the body. It can also be used to treat carbon monoxide poisoning under norma baric or hyper baric conditions. In this case, the fresh gas would contain a higher concentration of oxygen than ambient air, for example, 100% $O_2$, and the reserve gas will contain approximately 5.6% $CO_2$ and a high concentration of oxygen, for example, 94% of $O_2$.

In another embodiment of the invention, a method of controlling $PCO_2$ in a patient at a predetermined desired level is provided comprising a breathing circuit which is capable of organizing exhaled gas so as to be preferentially inhaled during re-breathing when necessary by providing alveolar gas for re-breathing in preference to dead space gas. The preferred circuit in effecting this method includes a breathing port for inhaling and exhaling gas, a bifurcated conduit adjacent to the port. The bifurcated conduit has a first and a second conduit branches. The first conduit has a fresh gas inlet and a check valve allowing the passage of inhaled fresh gas to the port but closing during exhalation. The second conduit branch includes a check valve which allows passage of exhaled gas through the check valve but prevents flow back to the port. A fresh gas reservoir is located at the terminus of the first conduit branch, while an exhaled gas reservoir is located at the terminus of the second conduit branch. An interconnecting conduit having a check valve therein is located between the first and the second conduit branches to result in the fresh flow gas in the circuit equal to baseline minute ventilation minus ventilation of anatomic dead space for the patient. In the exhaled gas reservoir, the exhaled gas is preferably disposed nearest the open end thereof, and the alveolar gas is located proximate the end of the reservoir nearest the terminus of the second conduit branch, so that the shortfall differential of $PCO_2$ is made of alveolar gas being preferentially rebreathed, thereby preventing a change in the $PCO_2$ level of alveolar gas despite the increased minute ventilation.

It is important to set up the fresh gas flow to be baseline minute ventilation minus anatomic dead space ventilation. In this way, once it is desired to increase the minute ventilation, a slight negative pressure will exist in the interconnecting conduit during inhalation, opening its check valve and allowing further breathing beyond the normal level of ventilation to be supplied by previously exhaled gas.

The present invention also provides a method of enhancing the results of a diagnostic procedure or medical treatment. A circuit which is capable of organizing exhaled gas so as to provide to the patient preferential rebreathing of alveolar gas in preference to dead space gas is provided. The patient is ventilated when a rate greater than the fresh gas flow is desired, and when hypercapnia is desired to induce. The fresh gas flow is passively decreased to provide a corresponding increase in rebreathed gas. The hypercapnia is continuously induced until the diagnostic or medical procedure is complete. Examples of the medical procedure includes MRI, radiation treatment or the like.

The present invention can also be applied to treat or assist a patient, preferably human, during a traumatic event characterized by hyperventilation. A breathing circuit in which alveolar ventilation is equal to the fresh gas flow and increases in alveolar ventilation with increases in minute ventilation is prevented, is provided. The circuit is capable of organizing exhaled gas provided to the patient and preferential rebreathing alveolar gas in preference to dead space gas following ventilating the patient at a rate of normal minute ventilation, preferably approximately 5 L per minute. When desired, hypercapnia is induced to increase arterial $PCO_2$ and prevent the $PCO_2$ level of arterial blood from dropping. The normocapnia is maintained despite the ventilation is increased until the traumatic hyperventilation is complete. As a result, the effects of hyperventilation experienced during the traumatic event are minimized. This can be applied when a mother is in labor and becomes light headed or when the baby during the delivery is effected with the oxygen delivery to its brain being decreased as a result of contraction of the blood vessels in the placenta and fetal brain. A list of circumstances in which the method enhancing the diagnostic procedure results or the experience of the traumatic even are listed below.

Applications of the method and circuit includes:
1) Maintenance of constant $PCO_2$ and inducing changes in $PCO_2$ during MRI.
2) Inducing and/or marinating increased $PCO_2$:
   a) to prevent or treat shivering and tremors during labor, post-anesthesia, hypothermia, and certain other pathological states;
   b) to treat fetal distress due to asphyxia;
   c) to induce cerebral vasodilatation, prevent cerebral vasospasm, and provide cerebral protection following subarachnoid hemorrhage cerebral trauma and other pathological states;
   d) to increase tissue perfusion in tissues containing cancerous cells to increase their sensitivity to ionizing radiation and delivery of chemotherapeutic agents;
   e) to aid in radio diagnostic procedures by providing contrast between tissues with normal and abnormal vascular response; and
   f) protection of various organs such as the lung, kidney and brain during states of multi-organ failure.
3) Prevention of hypocapnia with $O_2$ therapy, especially in pregnant patients.
4) Other applications where $O_2$ therapy is desired and it is important to prevent the accompanying drop in $PCO_2$.

By carrying out the above method and preferably with the above circuit, an improved method of creating MRI images is disclosed to maintain a constant $PCO_2$ and induce changes in that $PCO_2$ level during the MRI procedure in order to facilitate improvement in the quality of the images being obtained. The prior art Mapleson D and E circuits predictably may work with the method of the present invention as well as a standard circuit with the carbon dioxide filter bypassed or removed; however fresh gas will be wasted and the efficiency would be reduced.

A method of delivering to a patient, preferably human, inhaled drugs such as gases, vapors or suspensions of solid particles, particles or droplets, for example, nitric oxide, anesthetic vapors, bronchodilators or the like, using the above circuit to increase the efficiency of delivery allows the quantification of the exact dose.

A method of delivering to a patient, preferably human, pure oxygen is provided. The circuit described above increases the efficiency of delivery because all the fresh gas is inhaled by the patient, or to deliver the oxygen to the patient in a more predictable way, allowing the delivery of a precise concentration of oxygen.

When minute ventilation minus anatomical dead space ventilation is greater than or equal to fresh gas flow, the above circuit prevents loss of fresh gas and ensures that the patient receives all the fresh gas independent of the pattern of breathing since fresh gas alone enters the fresh gas reservoir, and exhaled gas enters its own separate reservoir. The fresh gas reservoir bag is large enough to store fresh gas for 5–10 seconds or more of reduced ventilation or total apnea, ensuring that even under these circumstances fresh gas will not be lost. The preferred circuit prevents rebreathing at a minute ventilation equal to the fresh gas flow because the check valve in the interconnecting conduit does not open to allow rebreathing of previously exhaled gas unless a negative pressure exist on the inspiratory side of the conduit of the circuit. Also, when minute ventilation exceeds the fresh gas flow, a negative pressure occurs in the inspiratory conduit, opening the conduit's check valve. The circuit provides that after the check valve opens, alveolar gas is rebreathed in preference to dead space gas because the interconnecting conduit is located such that exhaled alveolar gas will be closest to it and dead space gas will be further from it. When the fresh gas flow is equal to $VE-V_{Dan}$, the volume of rebreathed gas will ventilate the anatomical dead space only, leaving the alveolar ventilation unchanged. The exhaled gas reservoir is preferably sized at 3 L which is well in excess of the volume of an individual's breath, therefore it is unlikely that the patient shall be able to breathe any room air entering via the opening at the end of the exhaled gas reservoir.

The basic approach of preventing a decrease in $PCO_2$ with increased ventilation is similar to that of the non-rebreathing system. In brief, only the fresh gas contributes to alveolar ventilation ($V_A$) which establishes the gradient for $CO_2$ elimination. All gas breathed in excess of the fresh gas entering the circuit, or the fresh gas flow, is rebreathed gas. The terminal part of the exhaled gas contains gas that has been in equilibrium with arterial blood and hence has a $PCO_2$ substantially equal to arterial blood. The Fisher (WO98/41266) patent teaches that the closer $PCO_2$ in the inhaled gas to $PvCO_2$, the less the effect on $CO_2$ elimination. Yet, it would not maintain a constant $PaCO_2$ as $V_E$ increases. The present invention discloses that the greater the ventilation of gas with a $PCO_2$ equal to $PvCO_2$, the closer the $PaCO_2$ gets to $PvCO_2$. The present invention also discloses that when $PCO_2$ of inhaled gas is substantially equal to $PaCO_2$, increased ventilation will not tend to change the $PaCO_2$. Since the terminal part of the exhaled gas contains gas that has been in equilibrium with arterial blood and hence has a $PCO_2$ substantially equal to arterial blood, the $PaCO_2$ will be unchanged regardless of the extent of rebreathing.

With the use of the circuit of the present invention:
1. All of the fresh gas is inhaled by the subject when minute ventilation minus anatomical dead space is equal to or exceeds fresh gas flow.
2. The "alveolar gas" is preferentially rebreathed when minute ventilation minus anatomical dead space exceeds the fresh gas flow.
3. When minute ventilation minus anatomical dead space is equal to or greater than fresh gas flow, all the fresh gas contributes to alveolar ventilation.

In another embodiment of the invention, a method of establishing a constant flow of fresh gas in the form of atmospheric air forced as a result of breathing efforts by the patient, but independent of the extent of ventilation, is provided. The flow is delivered into a breathing circuit such as that taught by Fisher et al., (non-rebreathing) designed to keep the $PCO_2$ constant by providing expired gas to be inhaled when the minute ventilation exceeds the flow of fresh gas. Furthermore, there is provided a compact expired gas reservoir capable of organizing exhaled gas so as to be preferentially inhaled during rebreathing when necessary by providing alveolar gas for re-breathing in preference to dead space gas. The preferred circuit in effecting the above-mentioned method includes a breathing port for inhaling and exhaling gas, a bifurcated conduit adjacent to the port in substantially a Y-shape. The bifurcated conduit has a first and a second conduit branches. The first conduit has an atmospheric air inlet the flow through which is controlled by a resistance for example that being provided by a length of tubing, and a check valve allowing the passage of inhaled atmospheric air to the port but closing during exhalation. The second conduit branch includes a check valve which allows passage of exhaled gas through the check valve but prevents flow back to the port. An atmospheric air aspirator (AAA) is located at the terminus of the first conduit branch, while an exhaled gas reservoir of about 3 L in capacity is located at the terminus of the second conduit branch. The AAA comprises a collapsible container tending to recoil to open position. An interconnecting conduit having a check valve therein is located between the first and the second conduit branches. When minute ventilation minus anatomic dead space ventilation is equal to the rate of atmospheric air aspirated into the circuit, for example, 4 L per minute, atmospheric air enters the breathing port from the first conduit branch at a predetermined rate and preferably 4 L per minute. Meanwhile, the exhaled gas at a rate of 4 L per minute travels town to the exhaled gas reservoir. When it is desirable for the minute ventilation to exceed the fresh gas flow, for example, 4 L per minute, the patient will inhale expired gas retained in the expired gas reservoir through the interconnecting conduit at a rate making up the shortfall of the atmospheric air.

While setting the fresh gas flow to maintain a desired $PCO_2$, it is important to set up the atmospheric air aspirator be allowed to first be depleted of gas until it just empties at the end of the inhalation cycle. In this way, once it is desired to increase the minute ventilation, the increased breathing effort required to do so will further decrease the sub-atmospheric pressure in the first conduit branch, being the inspiratory limb, and open the check valve in the interconnecting conduit to allow further breathing of gas beyond the level of ventilation supplied by the volume of atmospheric air aspirated into the circuit during the entire breathing cycle.

The circuit of the present invention is particularly applicable when atmospheric air is a suitable form of fresh gas and when it is inconvenient or impossible to access a source of compressed gas or air pump to provide the fresh gas flow. During mountain climbing or working at high altitude, some people tend to increase their minute ventilation to an extent greater than that required to optimize the alveolar oxygen concentration. This will result in an excessive decrease in $PCO_2$ which will in turn result in an excessive decrease in flood flow and hence oxygen delivery to the brain. By using the above circuit at high altitude a limit can be put on the extent of decrease in $PCO_2$ and thus maintain the oxygen delivery to the brain in the optimal range.

During resuscitation of an asphyxiated newborn or an adult suffering a cardiac arrest, the blood flow through the lungs is remarkably slow during resuscitation attempts. Even normal rates of ventilation may result an excessive elimination of $CO_2$ from the blood. As the blood reaches brain, the low $PCO_2$ may constrict the blood vessels and limit the potential blood flow to the ischemic brain. By attaching the isocapnia circuit provided by the invention to the gas inlet port of a resuscitation bag and diverting all expiratory gas to the expiratory gas reservoir bag, the decrease of $PCO_2$ would be limited.

The isocapnia circuit of the present invention can be applied to enhance the results of a diagnostic procedure or a medical treatment by providing a circuit without a source of forced gas flow and being capable of organizing exhaled gas. With the circuit, preferential rebreathing of alveolar gas in preference to dead space gas is provided when the patient is ventilating at a rate greater than the rate of atmospheric air aspirated, and when inducing hypercapnia is desired. By decreasing the rate of aspirated atmospheric air, a corresponding increase in rebreathed gas is passively provided to prevent the $PCO_2$ level of arterial blood from dropping despite increase in minute ventilation. The step of inducing hypercapnia is continued until the diagnostic or medical therapeutic procedure is complete. The results of the diagnostic or medical procedure are thus enhanced by carrying out the method in relation to the results of the procedure had the method not been carried out. Examples of such procedures include MRI or preventing spasm of brain vessels after brain hemorrhage, radiation treatments or the like.

The present invention can also be applied to treat or assist a patient, preferably human, during a traumatic event characterized by hyperventilation. A circuit that does not require a source of forced gas flow, in which alveolar ventilation is equal to the rate of atmospheric air aspirated and increases in alveolar ventilation with increases in minute ventilation is prevented, is provided. For example, the isocapnia circuit as described above, is capable of organizing exhaled gas provided to the patient preferential rebreathing alveolar gas in preference to dead space gas following ventilating the patient at a rate of normal minute ventilation, preferably approximately 5 L per minute. When desired, hypercapnia is induced to increase arterial $PCO_2$ and prevent the $PCO_2$ level of arterial blood from dropping. The normocapnia is maintained despite the ventilation being increased until the traumatic hyperventilation is complete. As a result, the effects of hyperventilation experienced during the traumatic event are minimized. This can be applied when a mother is in labor and becomes light headed or the baby during the delivery is effected with the oxygen delivery to its brain being decreased as a result of contraction of the blood vessels in the placenta and fetal brain. A list of circumstances in which the method enhancing the diagnostic procedure results or the experience of the traumatic even are listed below.

Applications of the method and circuit includes:
1) Maintenance of constant $PCO_2$ and inducing changes in $PCO_2$ during MRI.
2) Inducing and/or marinating increased $PCO_2$:
   a) to prevent or treat shivering and tremors during labor, post-anesthesia, hypothermia, and certain other pathological states;
   b) to treat fetal distress due to asphyxia;
   c) to induce cerebral vasodilatation, prevent cerebral vasospasm, and provide cerebral protection following subarachnoid hemorrhage cerebral trauma and other pathological states;
   d) to increase tissue perfusion in tissues containing cancerous cells to increase their sensitivity to ionizing radiation and delivery of chemotherapeutic agents;
   e) to aid in radio diagnostic procedures by providing contrast between tissues with normal and abnormal vascular response; and
   f) protection of various organs such as the lung, kidney and brain during states of multi-organ failure.
3) Prevention of hypocapnia with $O_2$ therapy, especially in pregnant patients.
4) Other applications where $O_2$ therapy is desired and it is important to prevent the accompanying drop in $PCO_2$.

When minute ventilation is greater than or equal to the rate of atmospheric air aspirated, the above-mentioned preferred circuit ensures that the patient receives all the atmospheric air aspirated into the circuit, independent of the pattern of breathing; since atmospheric air alone enters the fresh gas reservoir and exhaled gas enters its own separate reservoir and all the aspirated air is delivered to the patient during inhalation before rebreathed exhaled gas. The atmospheric air aspirator preferably large enough not to fill to capacity during prolonged exhalation, when the total minute ventilation exceeds the rate of atmospheric air aspiration ensuring that under these circumstances atmospheric air continues to enter the circuit uninterrupted during exhalation. The preferred circuit prevents rebreathing at a minute ventilation equal to the rate of air being aspirated into the atmospheric air aspirator because the check valve in the interconnecting conduit does not open to allow rebreathing of previously exhaled gas unless a sub-atmospheric pressure less than that generated by the recoil of the aspirator exists on the inspiratory side of the conduit of the circuit. The circuit provides that after the check valve opens, alveolar gas is rebreathed in preference to dead space gas because the interconnecting conduit is located such that exhaled alveolar gas contained in the tube conducting the expired gas into the expiratory reservoir bag will be closest to it and dead space gas will be mixed with other exhaled gases in the reservoir bag. In the preferred embodiment, the exhaled gas reservoir is preferably sized at about 3 L which is well excess of the volume of an individual's breath. When the patient inhales gas from the reservoir bag, the reservoir bag collapses to displace the volume of gas extracted from the bag, minimizing the volume of atmospheric air entering the bag.

The basic approach of the present invention to prevent a decrease in $PCO_2$ with increase ventilation is to arrange that the fresh gas enters, the circuit at a rate equal to the desired minute ventilation minus anatomic dead space ventilation. In brief, breathing only fresh gas contributes to alveolar ventilation ($V_A$) which establishes the gradient for $CO_2$ elimination. All gas breathed in excess of the fresh gas entering the circuit, or the fresh gas flow, is rebreathed gas. The closer the partial pressure of carbon dioxide in the inhaled gas to that of arterial blood, the less the effect on $CO_2$ elimination. With increased levels of ventilation, greater volumes of previously exhaled gas are breathed. The rebreathed gas has a $PCO_2$ substantially equal to that of arterial blood, thus contributing little if anything to alveolar ventilation, and allowing the $P_{ET}CO_2$ and $PaCO_2$ to change little.

Further, if the fresh gas flow is equal to the minute ventilation minus the anatomic dead space ventilation, when minute ventilation is equal to or exceeds the rate of atmospheric air aspirated into the circuit, then all of the delivered fresh gas remains constant and equal to the resting alveolar ventilation. The "alveolar gas" is preferentially rebreathed when minute ventilation exceeds the fresh gas flow. These, as well as other features of the present invention will become more evident upon reference to the drawings and detailed description of the invention.

BRIEF DESCRIPTION OF THE DRAWINGS

FIG. 3 illustrates schematically the simple non-rebreathing circuit in one embodiment added to portions of the circle anaesthetic circuit shown schematically in FIG. 2, illustrating modifications of the circuit shown schematically in FIG. 1 for use with the circuit shown in FIG. 2;

FIG. 4A illustrates the structure shown in FIG. 3 combined with the structure shown in FIG. 2;

FIG. 9 is a schematic view of the portable circuit of the invention; and

FIG. 10 is a schematic view of the lungs illustrating anatomical dead space in relation to alveolar dead space.

DETAILED DESCRIPTION OF THE INVENTION

Figure 1:
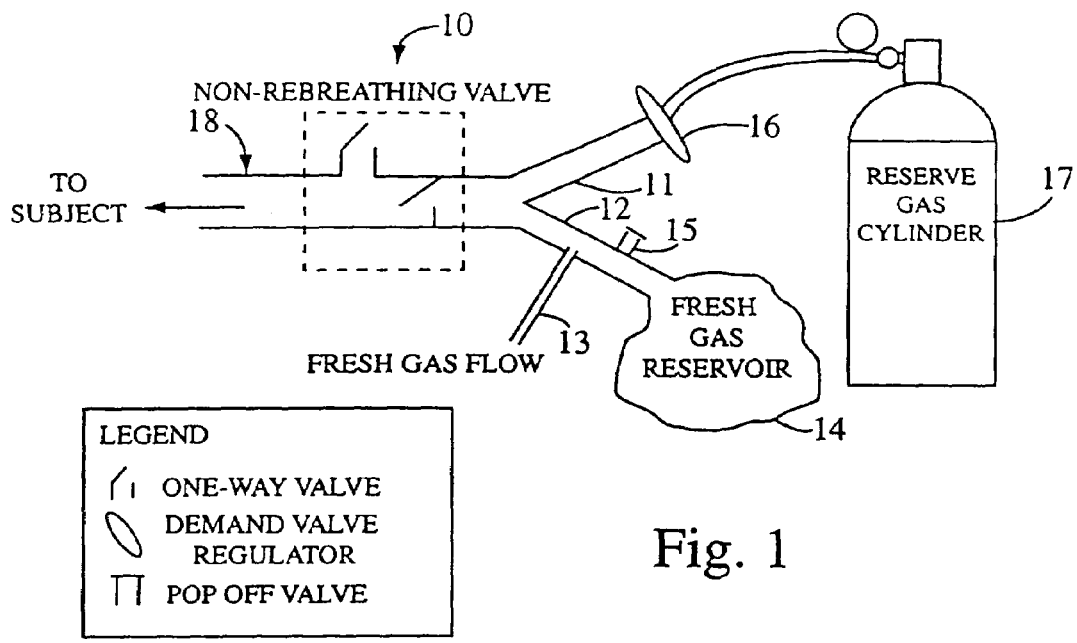
FIG. 1 illustrates schematically the nature of the simple non-rebreathing circuit and components which enable the patient to recover more quickly from vapor anaesthetics or other volatile agents. The device enables the arterial or end-tidal $PCO_2$ to remain relatively constant despite increase in minute ventilation which thereby permits faster elimination of the vapor anaesthetic or other volatile compounds.

PCT Application No. WO98/41266 filed by Joe Fisher (WO98/41266) teaches a method of accelerating the resuscitation of a patient which has been anaesthetized by providing the patient with a flow of fresh gas (FGF) and a source of reserve gas is expressly incorporated herein by reference. As thought in WO98/41266, when the patient breathes at a rate less than or equal to the fresh gas flowing into the circuit, all of the inhaled gas is made up of fresh gas. When the patient's minute ventilation exceeds the fresh gas flow, the inhaled gas is made up of all of the fresh gas and the additional gas is provided by "reserve gas" with a composition similar to the fresh gas but with $CO_2$ added such that the concentration of $CO_2$ in the reserve gas of about 6% is such that its partial pressure is equal to the partial pressure of $CO_2$ in the mixed venous blood. At no time while using this method will the patient rebreathe gas containing anaesthetic. In order to accelerate the resuscitation of the patient, a source of fresh gas is provided for normal levels of minute ventilation, typically 5 L per minute and a supply of reserve gas is provided for levels of ventilation above 5 L per minute wherein the source of reserve gas includes approximately 6% carbon dioxide having a $PCO_2$ level substantially equal to that of mixed venous blood.

Although Fisher's WO98/41266 method prevents significant variations in $P_{ET}CO_2$, it cannot keep $PCO_2$ precisely constant as a result of two imperial approximations in the method:

a) Setting FGF equal to the baseline minute ventilation as Fisher taught is excessive to keep the $PaCO_2$ from decreasing, since with increased ventilation, fresh gas from the anatomic dead space enters the alveoli providing increased alveolar ventilation which tends to lower $PaCO_2$.

b) Setting $PrgCO_2$ substantially equal to $PvCO_2$ prevents the elimination of $CO_2$ and tends to increase $PaCO_2$ towards $PrgCO_2$ as ventilation increases.

The proof assumes the same circuit described by Fisher, where a flow of fresh gas with a $PCO_2$ of 0 is set equal to Verest, and the balance of $V_E$ consists of reserve gas with a $PCO_2$ of $PrgCO_2$. This proof will show that $PrgCO_2$ should be equal to $PaCO_2$, and not to $PvCO_2$ as previously approximated in order for $P_{ET}CO_2$ to remain constant for any increase in $V_E$.

In pending application (Fisher I A, Vessely A., Sasano H., Volyesi G., Tesler J.: entitled Improved Rebreathing Circuit for Maintaining Isocapnia), filed in Canada March 2000 and in the USA in October 2000 as Ser. No. 09/676,899, the disclosure of which is expressly incorporated herein by reference) there is described a method of simplifying the circuit taught by Fisher (WO98/41266), wherein the reserve gas may be replaced by previously exhaled gas. The first filed Fisher application teaches that the fresh gas flow is set equal to minute ventilation to prevent change in $P_{ET}CO_2$ and $PaCO_2$. This is not optimal to prevent changes $P_{ET}CO_2$ and $PaCO_2$ since as minute ventilation increases, the fresh gas previously residing in the trachea exhaled without engaging in gas exchange can then be inhaled into the alveoli and hence adds to gas exchange and thus $P_{ET}CO_2$ and $PaCO_2$ which will equilibrate to a valve lower than those at rest.

However, the present invention teaches that to prevent changes in $P_{ET}CO_2$ and $PaCO_2$ the fresh gas flow should be substantially equal to the baseline ventilation minus the anatomic dead space ventilation.

Pending Canadian application Serial No. 2,340,511 filed by Fisher on Mar. 31, 2000 entitled A Portable Partial Rebreathing Circuit to Set and Stabilize End Tidal and Arterial $PCO_2$ Despite Varying Levels of Minute Ventilation which is also incorporated herein by reference describes a circuit a circuit that exploits the same principle in maintaining $PCO_2$ constant; however, it replaces the fresh gas reservoir bag with a substantially flexible container which is actively collapsed by the inspiratory effort of the patient during inspiration and passively expands during expiration drawing into itself and the circuit atmospheric air through a port provided for that purpose. The expiratory reservoir is provided with a flexible bag so that the volume of expired gas rebreathed is displaced by collapse of the bag rather than entrainment of atmospheric air, thus preventing the dilution of $CO_2$ in the expired gas reservoir.

It is the primary object of the present invention to form a portable circuit to reap the benefits of controlling the $PCO_2$ at a constant level and not having to incur the expense and inconvenience of supplying fresh gas. Furthermore the compact nature of the present invention will make its use practical outdoors, during physical activity and in remote environments, for example, for the resuscitation of newborns with air yet preventing an excessive decrease in $PCO_2$. In the prior art Fisher teaches that the total fresh gas flow into the bellows should be equal to minute ventilation. This again is not optimal to prevent changes $P_{ET}CO_2$ and $PaCO_2$ since as minute ventilation increases, the fresh gas previously residing in the trachea exhaled without an opportunity to engage in gas exchange can now be inhaled into the alveoli and add to gas exchange and thus $P_{ET}CO_2$ and $PaCO_2$ will equilibrate to a value lower than those at rest.

FIG. 1 shows a non-rebreathing circuit. In FIG. 1, a non-rebreathing valve 10 is connected distally to two ports 11 and 12. The port 12 is connected in parallel to a source of fresh gas 13 (which does not contain $CO_2$) and a fresh gas reservoir 14. A one-way pressure relief valve 15 prevents overfilling of the reservoir 14 by venting excess fresh gas. The port 11 is connected via a one-way valve 16 to a source of gas (containing $CO_2$) whose $PCO_2$ is equal approximately to that of the arterial $PCO_2$. The source of gas is called the reserve gas and denoted by a reference numeral 17. The non-rebreathing valve 10 is further connected to an exit port 18, from which the subject or the patient breathes.

Figure 5:
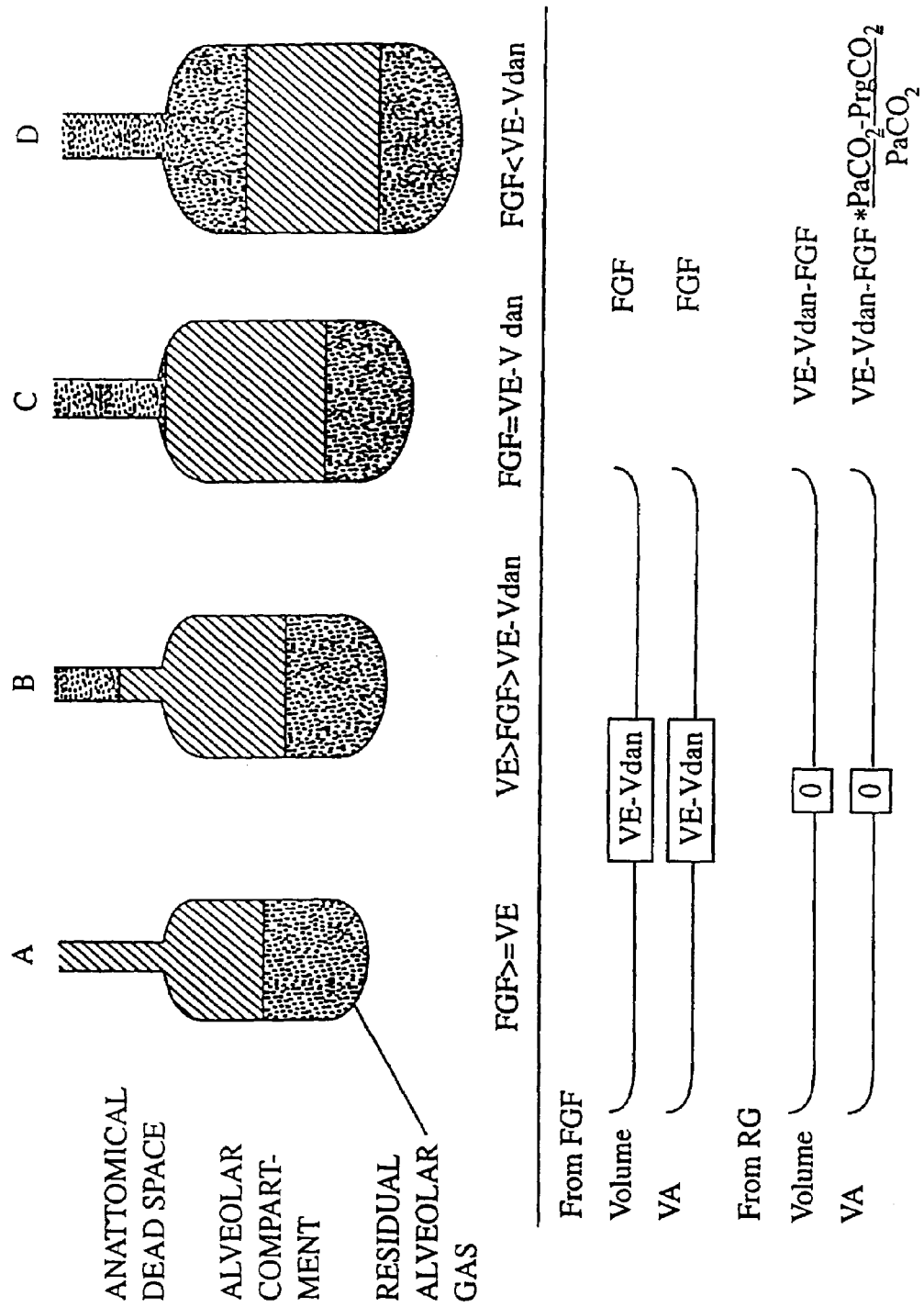
FIG. 5 depicts schematic representations of a lung at progressively increasing ventilations (A–D). Gas in the alveolar compartment of the lung participates in gas exchange, and thus can contribute to the elimination of $CO_2$, whereas gas in the anatomical dead space does not contribute to gas exchange. The hatched area indicates fresh gas; the stippled area indicates reserve gas.

FIG. 5 depicts schematic representations of a lung at progressively increasing ventilation (A–D). Gas in the alveolar compartment of the lung participates in gas exchange, and thus can contribute to the elimination of $CO_2$, whereas gas in the anatomical dead space does not contribute to gas exchange. The hatched area indicates fresh gas; the stippled area indicates reserve gas.

$V_E$ is the total amount of gas ventilation the lung, including both the alveolar compartment and the anatomical dead space. $V_D$an is the amount of gas ventilating just the anatomical dead space. Therefore, $V_E-V_D$an is the amount of gas available for ventilating the alveolar compartment, i.e., the amount of gas which can contribute to gas exchange (alveolar ventilation, $V_A$).

When $V_E-V_D$an is less than or equal to the fresh gas flow "FGF" from the source of fresh gas flow 13, only fresh gas (non-$CO_2$-containing gas) enters the alveolar compartment. When $V_E-V_D$an exceeds FGF, the reservoir 14 containing fresh non-$CO_2$-containing gas empties first and the balance of inhaled gas is drawn from the reserve gas 17 which contains a specific concentration of $CO_2$. If minute ventilation exceeds FGF, the difference between minute ventilation and fresh gas flow is made up of gas from the reserve gas source 17 which contains $CO_2$ at a partial pressure which, being substantially the same as that in the arterial blood, eliminates any gradient for diffusion of $CO_2$ between the two compartments. For example, if the FGF is 3 L per minute and the subject breathes at 5 L per minute or less, then the patient will inhale only non-$CO_2$-containing gas that comes from the source(s) of the fresh gas flow 13 and 14. In this case, a proportion of the fresh gas will ventilate the alveolar compartment (for example, at 4 L per minute) and the remainder of the fresh gas will ventilate the anatomical dead space (for example, at 1 L/min). Thus $V_E-V_D$an establishes the maximum potential alveolar ventilation ($V_A$).

Figure 8:
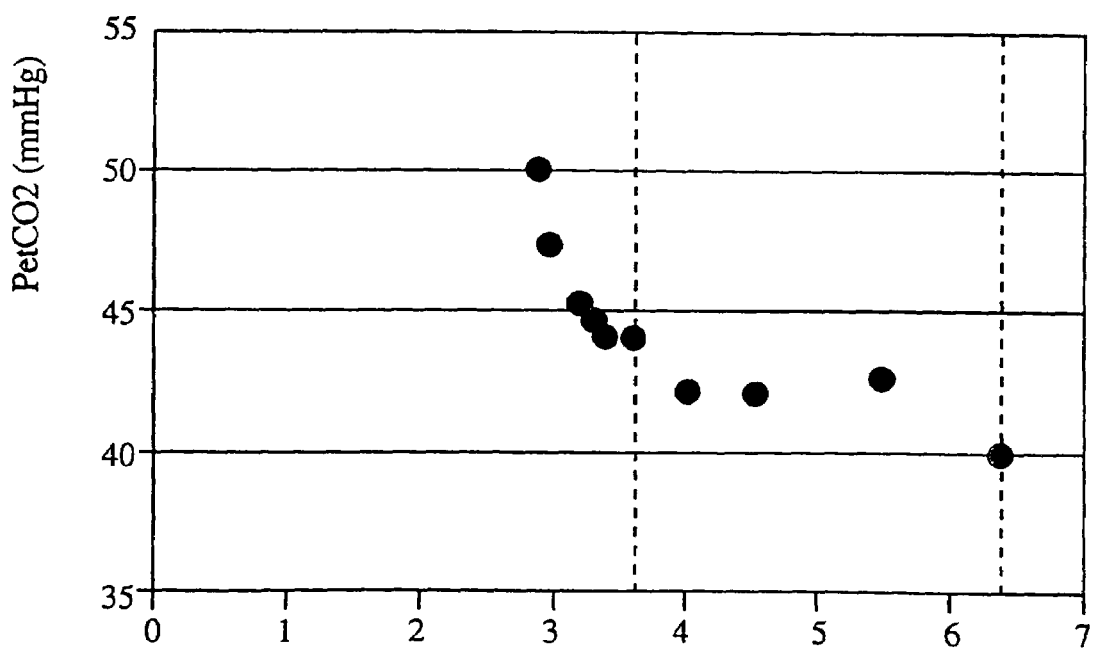
FIG. 8 illustrates a graph of how FGF flow may be slowly decreased affecting $P_{ET}CO_2$ exponentially in time.

When FGF is set exactly equal to $V_E-V_D$an (FIG. 5, panel C), fresh gas, and only fresh gas provides all the $V_A$. Therefore any increase in ventilation will result in reserve gas being the only additional gas drawn into the alveolar compartment. To set the FGF, after first approximately matching the fresh gas flow to $V_E$, the FGF can be slowly decreased, for example, in 200 mL/min decrements, without affecting the $PaCO_2$ (FIG. 8). This is because the initial decreases in FGF decrease only the amount of FGF ventilating the anatomical dead space, but not the alveolar compartment. At a certain point, which we term the "inflection point", any further decrease in FGF will decrease the volume of fresh gas ventilating the alveolar compartment per unit time and $PCO_2$ will begin to rise exponentially. The inflection point is the point at which FGF=$V_E-V_D$an, and represents the FGF required to maintain $PCO_2$ constant.

Figure 6:
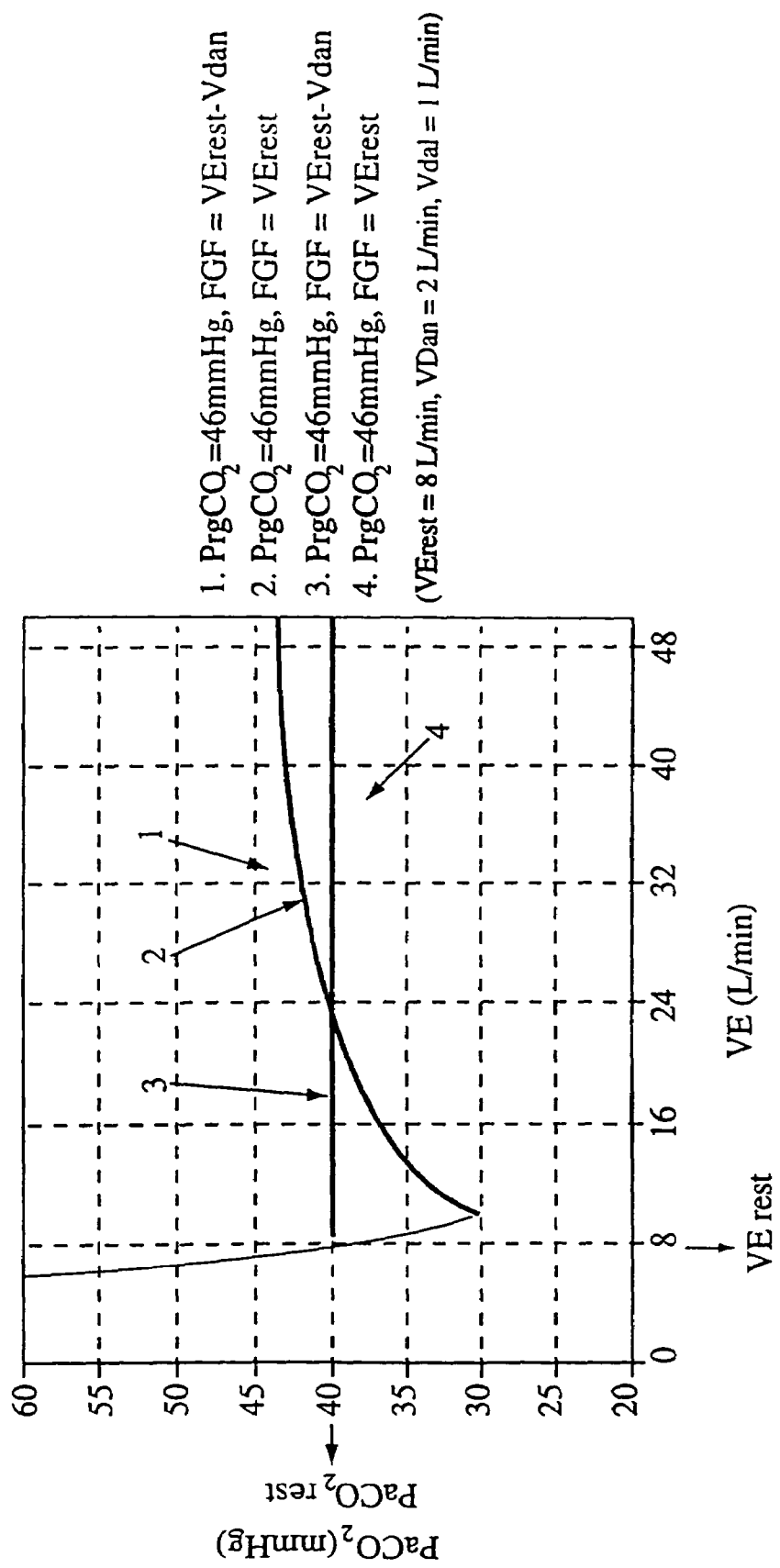
FIG. 6 illustrates a mathematical model used to calculate $PaCO_2$ as a function of minute ventilation.

Now considering the concentration of $CO_2$ which is required in the reserve gas in order to provide no ventilation. A mathematical model has been used to calculate the $PaCO_2$ as a function of minute ventilation (FIG. 6). Note that for each FGF and $PrgCO_2$ tested, the $PaCO_2$, as ventilation increases, approaches the $PCO_2$ of the reserve gas. This indicates that the appropriate reserve concentration is that equal to the desired $PaCO_2$. (Curves 3 and 4). A system of equations below confirms that the reserve gas $PCO_2$ must be equal to the arterial $PCO_2$.

When ventilation approaches infinity, the $PCO_2$ of the gas in the alveoli will approach the $PrgCO_2$. Since the $PaCO_2$ (for example 40 mmHg) is in equilibrium with the alveolar $PCO_2$, the $PaCO_2$ will approach the $PrgCO_2$ which has been set at $PvCO_2$ (46 mmHg), and thus will not be maintained at initial levels, for example 40 mmHg.

Clearly the $PrgCO_2$ cannot be set equal to $PvCO_2$. The present inventors have determined the $PrgCO_2$ should instead be set equal to $PaCO_2$ in order to maintain $PaCO_2$ unchanged at all levels of $V_E$ above resting $V_E$ (testing $V_E$). Although Fisher's method works well at low $V_E$, the present invention offer the following improvement which works well at all $V_E$, and in so doing provide a better explanation of the underlying physiology.

FGF shall equal resting minute ventilation minus anatomical dead space ventilation ($V_E-V_{Dan}$).

This proof assumes the same circuit described by Fisher, where a flow of fresh gas with a $PCO_2$ of 0 is set equal to $V_E$rest, and the balance of $V_E$ consists of reserve gas with a $PCO_2$ of $PrgCO_2$. This proof will show that $PrgCO_2$ should be equal to $PaCO_2$, and not to $PvCO_2$ as previously approximated in order for $P_{ET}CO_2$ to remain constant for any increase in $V_E$.

In the above and following description, $P_{ET}CO_2$ is defined as the end tidal partial pressure of carbon dioxide (mmHg);

$Prest_{ET}CO_2$ is the end tidal pressure of carbon dioxide (mmHg);

$PiCO_2$ is the inspired partial pressure of carbon dioxide (mmHg);

Pbar is the barometric pressure (mmHg);

$V_E$ is the minute ventilation (mL/min);

$VCO_2$ is the volume of $CO_2$ produced in 1 minute (mL/min);

$VrestCO_2$ is the volume of $CO_2$ produced at rest in 1 minute (mL/min);

Verest is the minute ventilation at rest;
n is the minute ventilation expressed as number of times minute ventilation at rest;

$n$ is equal to $V_E/V_E\text{rest}$, so that $V_E = n*V_E\text{rest}$ (1)

By specifying that VCO2 remains at VrestCO$_2$, so that VCO$_2$=VrestCO$_2$; and P$_{ET}$CO$_2$ remains at Prest$_{ET}$CO$_2$, so that P$_{ET}$CO$_2$=Prest$_{ET}$CO$_2$.

The difference between the inspired and expired PCO$_2$ (as a fraction of the barometric pressure) times the ventilation must be equal to the CO$_2$ produced by the body in a given period of time (for example 1 minute).

$(\text{Prest}_{ET}CO_2 - PiCO_2)/Pbar * V_E = VrestCO_2$ (2)

With Fisher's circuit, inspired PCO$_2$ can be calculated for any n. The inspired PCO$_2$ is an average of the PCO$_2$ of the fresh gas (0 mmHg) and the reserve gas (PrgCO$_2$), weighted by the relative volumes inspired:

$PCO_2 = (n-1)/n * PrgCO_2$ (3)

For example, at 4×V$_E$rest, inspired PCO$_2$ is ¾ reserve gas PCO$_2$, because reserve gas comprises ¾ of the total gas inspired, while the remaining ¼ is fresh gas which has a PCO$_2$ of 0.

Substitution of 1 and 3 into 2 gives $((P_{ET}CO_2 - (n-1)/n*PrgCO_2)/Pbar)$
$\quad *n*V_E\text{rest} = VrestCO_2)$ Solving for PrgCO$_2$, $P_{ET}CO_2 - (n-1)/n*PrgCO_2 = VrestCO_2*Pbar/(n*V_E\text{rest})$ $P_{ET}CO_2 - VrestCO_2*Pbar/(n*V_E\text{rest}) = (n-1)/n*PrgCO_2$ $(P_{ET}CO_2 - VrestCO_2*Pbar/(n*V_E\text{rest}))*n/(n-1) = PrgCO_2$ $PrgCO_2 = (\text{Prest}_{ET}CO_2 - VrestCO_2*Pbar/(n*V\text{rest}))*n/(n-1)$ (4)

Now, $(VCO_2/V_E)*Pbar = PrestETCO_2$ (5)

Solving (5) for V$_E$, we obtain $V_E = VCO_2*Pbar/\text{Prest}_{ET}CO_2$ (6)

Then at V$_E$rest, $V_E\text{rest} = VrestCO_2*Pbar/\text{Prest}_{ET}CO_2$ (7)

Substituting 7 into 4, we obtain, $PrgCO_2 = (\text{Prest}_{ET}CO_2 - VrestCO_2*Pbar/(n*$
$\quad(VrestCO_2*Pbar/\text{Prest}_{ET}CO_2))*n/(-1)$ (8)

Canceling like terms for numerator and denominator in 8, we obtain $PrgCO_2 = (\text{Prest}_{ET}CO_2 - \text{Prest}_{ET}CO_2/n)*n/(n-1)$ (9)

Factoring out Prest$_{ET}$CO$_2$ in (9), we obtain $PrgCO_2 = \text{Prest}_{ET}CO_2*(1 - 1/n)*n/(n-1)$ (10)

Factoring out n in (10), we obtain $PrgCO_2 = \text{Prest}_{ET}CO_2*((n-1)/n)*n/(n-1)$ (11)

Cancelling like terms from (11), $PrgCO_2 = \text{Prest}_{ET}CO_2$ (12)

Therefore, the reserve gas PCO$_2$ must be equal to the resting end-tidal PCO$_2$ in order for the condition to be met of end-tidal PCO$_2$ remaining constant with increased V$_E$.

This provides an additional advantage over Fisher's method, because the resting P$_{ET}$CO$_2$ can be obtained more readily than the PvCO$_2$. To maintain P$_{ET}$CO$_2$ constant, the PrgCO$_2$ can be set by simply measuring the concentration of CO$_2$ in gas sampled at end-expiration. If this is unknown, the PrgCO$_2$ can be set equal to the desired PaCO$_2$ (for example 40 mmHg). With higher and higher minute ventilation, the subject's PaCO$_2$ will approach the PrgCO$_2$, whatever it might have been initially. In this situation, preferably, the fresh gas flow would also be set equal to the required alveolar ventilation which would produce the desired arterial PCO$_2$. This could be empirically determined, or calculated from the alveolar gas equation.

Therefore, from the above it is shown that in order to make PaCO$_2$ independent of minute ventilation (FIG. 6), FGF should be set substantially equal to baseline minute ventilation minus anatomical dead space, and reserve gas PCO$_2$ should be set substantially equal to arterial PCO$_2$.

The present invention provides a new equation more fully and accurately describing what is happening than that of Fisher. PvCO$_2$ in Fisher's equation has been replaced with PaCO$_2$. V$_E$ in Fisher's equation has been replaced with V$_E$−V$_{Dan}$. Finally, an additional term has been added which describes the effect of the alveolar dead space. The alveolar dead space ventilation has the effect of decreasing the amount of fresh gas and reserve gas by the proportion of total ventilation of the alveolar compartment which it occupies.

$$V_A = \overline{1 - \frac{V_{D_a|V}}{V_E - V_{Dan}}} \leftrightarrow FGF + ((V_E - V_{Dan}) - FGF) \leftrightarrow \frac{-PaCO_2 - PrgCO_2}{PaCO_2}$$

Figure 2:
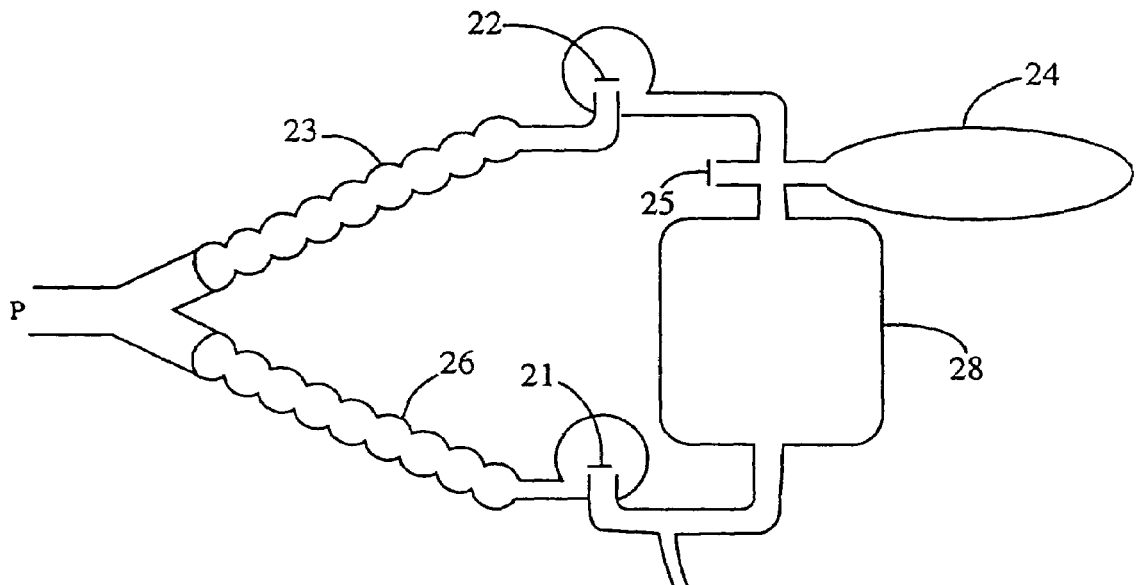
FIG. 2 illustrates schematically portions of a standard circle anaesthetic.

FIG. 2 shows the schematic of the standard anaesthetic circle circuit, spontaneous ventilation. When the patient exhales, the inspiratory valve 21 closes, the expiratory valve 22 opens and gas flows through the corrugated tubing making up the expiratory limb of the circuit 23 into the rebreathing bag 24. When the rebreathing bag 24 is full, the airway pressure-limiting (APL) valve 25 opens and the balance of expired gas exits through the APL valve 25 into a gas scavenger (not shown). When the patient inhales, the negative pressure in the circuit closes the expiratory valve 22, opens the inspiratory valve 21, and directs gas to flow through the corrugated tube making up the inspiratory limb of the circuit 26. Inspiration draws all of the gas from the fresh gas hose 27 and makes up the balance of the volume of the breath by drawing gas from the rebreathing bag 24. The gas from the rebreathing bag contains expired gas with CO$_2$ in it. The CO$_2$ is extracted as the gas passes through the CO$_2$ absorber 28 and thus is delivered to the patient (P) without CO$_2$ (but still containing exhaled anaesthetic vapor, if any).

A modification of the circuit as shown in FIG. 2 to allow hyperventilation of patient under anaesthesia is shown in FIG. 3.

Figure 4B:
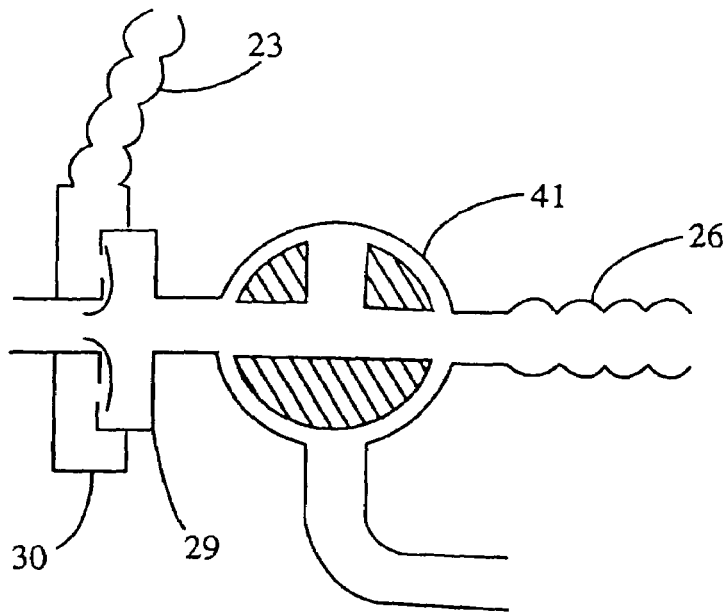
FIGS. 4B and 4C illustrate schematically close up portions of one portion of the structure shown in FIG. 4A in different positions.

The modification comprises:

1. A circuit which acts functionally like a standard self inflating bag (such as made by Laerdal), having:

a) a non-rebreathing valve 29, such as valve #560200 made by Laerdal, that functions during spontaneous breathing as well as manually assisted breathing;

b) an expired gas manifold 30, such as the expiratory deviator #850500, to collect expired gas and direct it to a gas scavenger system (not shown) or to the expiratory limb of the anaesthetic circuit (FIG. 4);

c) a self inflating bag 31 whose entrance is guarded by a one-way valve 32 directing gas into the self inflating bag 31.

2. A source of fresh gas (i.e., not containing vapor) 33 e.g. oxygen or oxygen plus nitrous oxide with a flow meter (32).

3. A manifold 34 with 4 ports:
   a) port 35 for input of fresh gas 33;
   b) port 36 for a fresh gas reservoir bag 37;
   c) port which is attached a one-way inflow valve 38 that opens when the pressure inside the manifold is 5 cm $H_2O$ less than atmospheric pressure, such as Livingston Health Care Services part #9005, (assuring that all of the fresh gas is utilized before opening);
   d) a bag of gas 39 whose $PCO_2$ is equal to approximately to that of the arterial $PCO_2$ connected to inflow valve 38 (alternatively, the valve and gas reservoir bag can be replaced by a demand regulator, such as Lifetronix MS91120012, similar to that used in SCUBA diving, and a cylinder of compressed gas);
   e) a port to which a one-way outflow valve 40, such as Livingston Health Care Services catalog part #9005, that allows release of gas from the manifold to atmosphere when the pressure in the manifold is greater than 5 cm $H_2O$.

The operation method of the anaesthetic circuit is shown as FIG. 4A. The distal end of the nonrebreathing valve 29 (Laerdal type) as shown in FIG. 3 is attached to the patient.

Figure 4C:
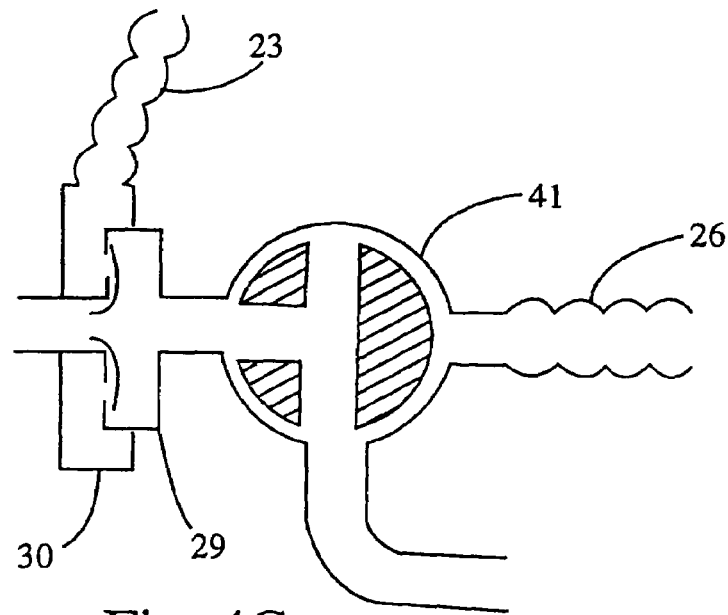

The proximal port of the nonrebreathing valve 39 is attached to a 3 way respiratory valve 41 which can direct inspiratory gas either from the circle anaesthetic circuit (FIG. 4B) or from the new circuit (FIG. 4C). The expiratory manifold 30 of the self inflating bag's non rebreathing valve 29 is attached to the expiratory limb of the anaesthetic circuit 23. Regardless of the source of inspired gas, exhalation is directed into the expiratory limb of the anaesthetic circuit.

To maximize the elimination of anesthetic vapor from the patient's lung, the 3-way respiratory stopcock 41 is turned such that the patient inspiration is from the new circuit (FIG. 4C). Thus inspired gas from the very first breath after turning the 3-way valve onward contains no vapor, providing the maximum gradient for anaesthetic vapor elimination.

An increased breathing rate will further enhance the elimination of vapor from the lung. If breathing spontaneously, the patient can be stimulated to increase his minute ventilation by lowering the FGF 42 thereby allowing $PCO_2$ to rise. Using this approach the $PCO_2$ will rise and plateau independent of the rate of breathing, resulting in a constant breathing stimulus. All of the ventilation is effective in eliminating vapor.

If the patient is undergoing controlled ventilation, he can also be hyperventilated with the self-inflating bag 31. In either case, the patient's $PCO_2$ will be determined by the FGF 42. As long as the FGF remains constant, the $PCO_2$ will remain constant independent of the minute ventilation.

Conventional servo-controlled techniques designed to prevent changes in $PCO_2$ with hyperpnea are less affected by changes in $CO_2$ production than the circuit; however, they have other limitations. The assumption that detected changes in $P_{ET}CO_2$ are due to a change in $PaCO_2$ is not always warranted 34. Small changes in ventilatory pattern can "uncouple" $P_{ET}CO_2$ from $PaCO_2$, resulting in $P_{ET}CO_2$ being an inappropriate input for the control of $PaCO_2$. For example, a smaller $V_T$ decreases $V_A$ (which tends to increase $PaCO_2$) but will also decrease $P_{ET}CO_2$, causing a servo-controller to respond with an inappropriate increase in inspired $CO_2$. Even under ideal conditions, a servo-controlled system attempting to correct for changes in $P_{ET}CO_2$ cannot predict the size of an impending $V_T$ in a spontaneously breathing subjecting and thus deliver the appropriate $CO_2$ load. If in an attempt to obtain fine control the gain in a servo-control system is set too high, the response becomes unstable and may result in oscillation of the control variable 31. Conversely, if the gain is set too low, compensation lags 39. Over-damping of the signal results in the response never reaching the target. To address these problems, servo-controllers require complex algorithms 36 and expensive equipment.

When $CO_2$ production is constant, the circuit has the theoretical advantage over servo-controlled systems in that it provides passive compensation for changes in V. This minimizes changes in $V_A$, pre-emptying the need for subsequent compensation. Maintenance of a nearly constant $V_A$ occurs even during irregular breathing, including brief periods when V is less than the FGF. Under this circumstance, excess FGF is stored in the fresh gas reservoir and subsequently contributes to $V_A$ when ventilation exceeds FGF.

When $CO_2$ production increases during hyperventilation, as would occur with increased work of breathing or exercise, our method requires modification. To compensate, additional $V_A$ can be provided either by increasing FGF or by lowering the $PCO_2$ of the reserve gas below the $PvCO_2$.

As such, a simple circuit that disassociates $V_A$ from V has been described. It passively minimizes increases in VA that would normally accompany hyperventilation when $CO_2$ production is constant. It can be modified to compensate for increases in $CO_2$ production. The circuit may form the basis for a simple and inexpensive alternative to servo-controlled systems for research and may have therapeutic applications.

Figure 7:
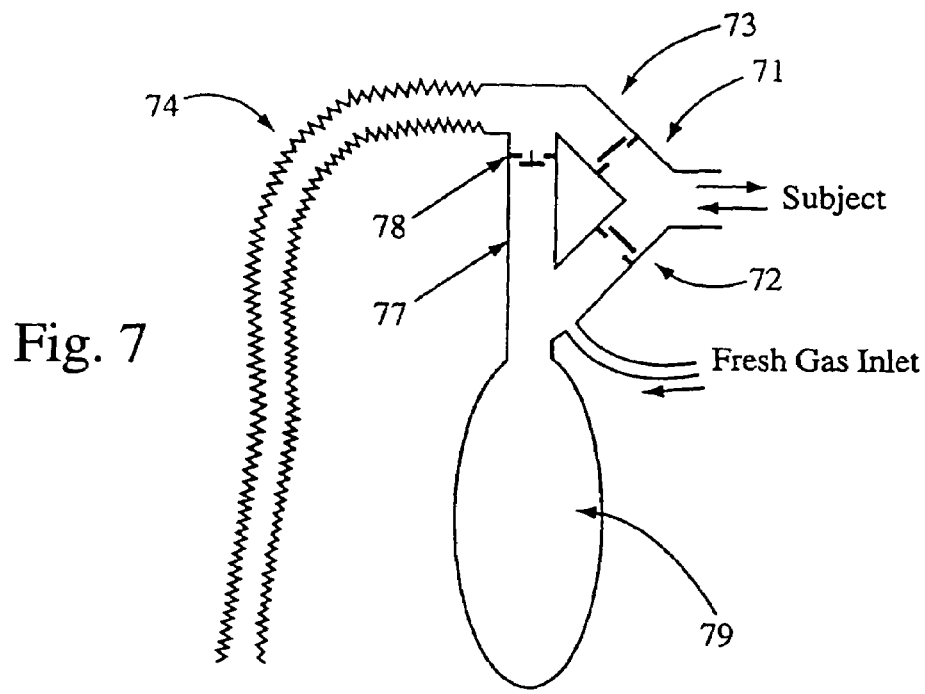
FIG. 7 illustrates schematically the nature of the simple breathing circuit and components enabling the $PCO_2$ to remain constant despite in crease in minute ventilation.

Referring to FIG. 7, the patient breathes through one port of a Y-piece 71. The other 2 arms of the Y-piece contain 1-way valves. The inspiratory limb of the Y-piece contains a one-way valve, the inspiratory valve 72 which directs gas to flow towards the patient when the patient makes an inspiratory effort, and acts as a check valve preventing flow in the opposite direction during exhalation. The other limb of the Y-piece 71, the expiratory limb, contains a one-way valve, the expiratory valve 73, positioned such that it allows gas to exit the Y-piece 71 when the patient exhales, and also acts as a check valve to prevent flow towards the patient when the patient inhales. Immediately distal to the expiratory limb of the Y-piece is attached large bore tubing 74, termed "reservoir tube" that is open at its distal end 75. The reservoir tube is preferably greater then 22 mm in diameter, and its length is such that the total volume of the tubing is about or greater than 3 L when it is being used for an average (70 kg) adult. Larger volumes of reservoir tubing will be required for larger subjects and vice versa. The inspiratory port is connected to a source of fresh gas 76, i.e., gas not containing $CO_2$, flowing into the circuit at a fixed rate and a fresh gas reservoir bag 79 of about 3 L in volume. A bypass conduit 77 connects the expiratory limb and the inspiratory limb. The opening of the conduit to the expiratory limb is preferably as close as possible to the expiratory one-way valve. This conduit contains a one-way valve 78 allowing flow from the expiratory to the inspiratory limb. The conduit's one-way valve 78 allowing flow from the expiratory to the inspiratory limb. The conduit's one-way valve 78 requires an opening pressure differential across the valve slightly greater than that of the inspiratory valve. In this way, during inspiration, fresh gas, consisting of fresh gas flow and the contents of the fresh gas reservoir bag, is preferentially drawn from the inspiratory manifold.

When the patient's minute ventilation less anatomical dead space is equal to or less than the FGF, only fresh gas (FG) is breathed. During exhalation FG accumulates in the FG reservoir. During inhalation fresh gas glowing into the circuit and the contents of the fresh gas reservoir are inhaled. When minute ventilation less anatomical dead space exceeds FGF, on each breath, FG is breathed until the FG reservoir is emptied. Additional inspiratory efforts result in a decrease in pressure on the inspiratory side of the current. When this pressure differential across the valve of the bypass conduit exceed its opening pressure, the one-way valve opens and exhaled gas is drawn back from the expired gas reservoir into the inspiratory limb of the Y-piece and hence to the patient. The last gas to be exhaled during the previous breath, termed "alveolar gas" is the first to be drawn back into the inspiratory limb and inhaled (rebreathed) by the subject.

A method of measuring the anatomical dead space can be provided. The fresh gas flow can be set equal to the minute ventilation less the anatomical dead space ventilation $V_{Dan}$. Fresh gas flow should initially be set approximately equal to the resting minute ventilation. Fresh gas flow can be slowly decreased, for example, 200 mL/min at a time. $P_{ET}CO_2$, will remain flat initially, and at some point will begin to rise exponentially. This can be seen in FIG. 8, in which a human subject breathes through the circuit while fresh gas flow was decreased in steps. This point is defined as the "inflection point". The FGF at the inflection point is equal to $V_E-V_D$an. It is apparent that this circuit can therefore be used to measure anatomical dead space as the difference between resting ventilation and the inflection point, divided by the respiratory frequency $V_{Dan}=(V_E-VFGF$ at inflection point), and anatomical dead space=$(V_E-FGF$ at inflection point)/f. Those skilled in the art will recognize that there are other ways to use this circuit to measure dead space for example measuring the resting $V_E$ and $P_{ET}CO_2$, asking the subject to hyperventilate and then progressively decreasing the fresh gas glow until resting $P_{ET}CO_2$ is reached. Because the rebreathing circuit taught by Fisher works in the same way, it too can be used to measure anatomical dead space in this way. Other variations of using these circuits to measure anatomical dead space will be apparent to those skilled in the art. This method of measuring anatomical dead space can be used with any circuit where fresh gas flow limits alveolar ventilation under the conditions where all fresh gas flow is inhaled during breathing.

FIG. 9 shows a portable isocapna circuit. The patient or subject breathes (inhales and exhales) through one port of a Y-piece 91. The isocapnia circuit has another two ports in a form of two limbs of the Y-piece 91, and each of them comprises a one-way valve. One of the limbs with an inspiratory valve 92 functions as an inspiration port, while the other limb with an expiratory valve 93 functions as an expiration port. The inspiratory valve 92 directs gas to flow towards the patient when the patient makes an inspiratory effort, and acts as a check valve preventing flow in the opposite direction during exhalation. The expiratory valve 93 allows gas to exit the Y-piece 91 when the patient exhales, and also acts as a check valve to prevent flow towards the patient when the patient inhales. Immediately distal to the expiratory limb of the Y-piece 91, a large bore tubing termed "alveolar gas reservoir" 94 is attached. The alveolar gas reservoir 94 is contained in a pliable bag of about 3 L in volume. Bag 95, has a proximal end sealed around a proximal end of the alveolar gas reservoir 94. The expiratory gas reservoir bag 95 further has another tubing called the "exhaust tubing" 96 situated at a distal end where the expired gas exits to atmosphere 97. Thus arranged, most of the exhaust tubing 96 is contained in the expiratory gas reservoir bag 95, and which is sealed to the circumference of the exhaust tubing 96 at its distal end. Preferably, the exhaust tubing 96 has a diameter smaller than that of the alveolar gas reservoir 94. In one embodiment, the alveolar gas reservoir 94 is about 35 mm in diameter, and has a length to provide a total volume of about or greater than 0.3 while being applied to an average (70 kg) adult. Distal to the expiratory limb of the Y-piece 91, a large bore tubing termed "alveolar gas reservoir" 94 is attached. The alveolar gas reservoir 94 is contained in a pliable bag of about 3 L in volume. The pliable bag, named "expiratory gas reservoir bag" 95, has a proximal end sealed around a proximal end of the alveolar gas reservoir 94. The expiratory gas reservoir bag 95 further has another tubing called the "exhaust tubing" 96 situated at a distal end where the expired gas exits to atmosphere 97. Thus arranged, most of the exhaust tubing 96 is contained in the expiratory gas reservoir bag 95, and which is sealed to the circumference of the exhaust tubing 96 at its distal end. Preferably, the exhaust tubing 96 has a diameter smaller than that of the alveolar gas reservoir 94. In one embodiment, the alveolar gas reservoir 94 is about 35 mm in diameter, and has a length to provide a total volume of about or greater than 0.3 while being applied to an average (70 kg) adult.

The inspiratory limb opens into a cylindrical container comprising a rigid proximal end plate 98, a collapsible plicate tube 99 extending distally from the circumference of the proximate end plate 98, and a distal end rigid plate 110 sealing the distal end of the collapsible plicate tube 99. When not in use, the collapsible plicate tube 99 is kept open by the gravitation of the distal end rigid plate 110, and/or by the force of a spring 111 attached on the collapsible plicate tube 99, and/or by intrinsic recoil of the plicate tubing 99. The inspiratory limb is also open to the atmosphere by means of a nozzle 112, to which a tube 113 is attached. The rigid plate 110 is open to a nozzle 114, to which another tube 115 is attached. The proximal end plate 98 has a protuberance 116 pointing at the tube 115 that is aligned with the internal opening of the distal end plate nozzle 114. The combination of the proximal end plate 98, the collapsible plicate tube 99, the distal end rigid plate 110, the spring 111, the inspiratory limb nozzle 112, the tube 113 attached to the nozzle 112, the distal end plate nozzle 114, the tube 115 attached to the distal end plate nozzle 114 and the protuberance 116 are in aggregate as am "atmosphere air aspirator (AAA)". A bypass conduit 117 is further included in the Y-piece 91 to connect the expiratory limb and the inspiratory limb. The opening of the bypass conduit 117 is preferably as close as possible to the expiratory valve 93. The bypass conduit 117 has a one-way valve 118 allowing flow from the expiratory limb to the inspiratory limb only. The one-way valve 118 of the bypass conduit 117 requires an opening pressure differential slightly greater than the pressure difference between the inspiratory limb pressure and atmospheric pressure that is sufficient to collapse the plicate tube 99. In this way, during inspiration, atmosphere air contained in the atmospheric air aspirator and the air being continuously aspirated into the inspiratory limb is preferentially drawn from the inspiratory manifold.

Considering the above isocapnia circuit without the spring 111, the nozzle 114 on the distal end plate 114, or the internally directed protuberance 116, each inspiration drawn initially from the atmospheric air aspirator collapses the plicate tube 99 and approximates the distal end plate 110 to the proximal end plate 18 when the patient begins to breathe. As long as the plicate tube 99 is partially collapsed, there is a constant sub-atmospheric pressure in the inspiratory limb of the isocapnia circuit. The sub-atmospheric pressure creates a pressure gradient that draws the atmospheric air into the inspiratory limb of the isocapnia circuit through the nozzle 112 and the tube 113. When the minute ventilation of the subject is equal to or less than the intended flow of atmospheric air into the aspirator, only atmospheric air is breathed. During exhalation, atmospheric air accumulates in the aspirator. During inhalation, inspired gas consist of the contents of the atmospheric air aspirator and the atmospheric air flowing into the inspiratory limb through the nozzle 113. When the minute ventilation of the subject exceeds the net flow of the atmospheric air into the isocapnia circuit, air is breathed for each breath until the atmospheric air aspirator is collapsed. Additional inspiratory efforts result in an additional decrease in gas pressure on the inspiratory side of the isocapnia circuit.

When the pressure differential across the valve 118 of the bypass conduit 117 exceeds its opening pressure, the one-way valve 118 opens and the exhaled gas is drawn back from the expiratory reservoir bag 95 into the inspiratory limb of the Y-piece 91 and hence to the patient. To the extent that the opening pressure of the valve 118 is close to the pressure generated by the recoil of the atmospheric air aspirator, there will be little change in the flow of atmospheric air into the isocapnia circuit during inspiration after the atmospheric air aspirator has collapsed. The last gas to be exhaled during the previous breath, termed "alveolar gas", is retained in the alveolar gas reservoir 14 and is the first gas to be drawn back into the inspiratory limb of the isocapnia circuit and inhaled (rebreathed) by the patient. After several breaths, the rest of the expired gas from the expiratory gas reservoir bag 95 contains mixed expired gas. The mixed expired gas from the expiratory gas reservoir bag 95 replace the gas drawn from the alveolar gas reservoir 94 and provides the balance of the inspired volume required to meet the inspiratory effort of the patient. The greater restriction in the diameter of the second tube, that is, the exhaust tubing 96, than in the alveolar gas reservoir 94 results in the gas being drawn into the alveolar gas reservoir 94 being displaced by the collapse of the expiratory gas reservoir bag 95 in preference to drawing air from the ambient atmosphere. The exhaust tubing in the expiratory reservoir bag 96 provides a rout for exhaust of expired gas and acts as a reservoir for that volume of atmospheric air diffusing into the expiratory reservoir bag through the distal opening, tending to keep such atmospheric air separate from the mixed expired gas contained in the expiratory gas reservoir bag 95.

During exhalation and all of inhalation until the collapse of the atmospheric gas aspirator, the flow of atmospheric air into the circuit will remain constant. However, after the atmospheric air aspirator collapses the pressure gradient will increase. The effect of the increase in total flow will depend on the difference between the opening pressure of the bypass valve 118 and the recoil pressure of the atmospheric air aspirator times the fraction of the respiratory cycle when the atmospheric air aspirator is collapsed. If the fraction of the respiratory cycle when the atmospheric air aspirator is collapsed is great, as when there is a very great excess minute ventilation above the rate of atmospheric air aspiration, the atmospheric air aspirator can be modified adding a second port for air entry at, for example, the distal end plate nozzle 114. As a result, the total flow from the two ports provides the desired total flow of air into the circuit under the recoil pressure of the atmospheric air aspirator. When the atmospheric air aspirator collapses on inspiration, the second port 114 is occluded by the protuberance 116. The remaining port, that is, the nozzle 112, provides a greater resistance to air flow to offset the greater pressure gradient being that gradient required to open the bypass valve 118.

In the above embodiment, it is assumed that the gravitation acting on the distal plate 110 provides the recoil pressure to open the atmospheric air aspirator. The disadvantage to this configuration is that the distal end plate 110 must be heavy enough to generate the sub-atmospheric pressure. This may be too heavy to be supported by attachment to a face mask strapped to the face. Furthermore, movement such as walking or running or spasmodic inhalation will cause variations in the pressure inside the atmospheric air aspirator and hence variation in flow of air into the atmospheric air aspirator. In such cases, it is better to minimize the mass of the distal end plate 110 and use a different type of motive force to provide recoil symbolized by the spring 111.

Preferably the circuit as described above is installed in a case to render it fully portable. The case may include the appropriate number of capped ports to allow proper set up and use of the circuit.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

The invention claimed is:

1. An isocapnia circuit, comprising:
   an exit port, from which gases exit from the isocapnia circuit to a patient;
   a valve, permitting gases delivered to the exit port for the patient, but preventing gases from passing therethrough to the isocapnia circuit;
   a source of fresh gas, containing a physiologically insignificant amount of $CO_2$ in communication with the valve to be delivered to the patient;
   a fresh gas reservoir, in communication with the source of fresh gas flow for receiving excess fresh gas not breathed by the patient; and
   a reserve gas supply, in communication with the exit port through the valve and containing $CO_2$ having a $PCO_2$ approximately equal to $PCO_2$ in the arterial blood of the subject.

2. The isocapnia circuit of claim 1, wherein the source of gas, the fresh gas reservoir and the reserve gas supply are disposed on a side of the valve remote from the exit port.

3. The isocapnia circuit of claim 1, further comprises a pressure relief in communication with the source of fresh gas and the fresh gas reservoir.

4. The isocapnia circuit of claim 1, wherein the reserve gas supply comprises a demand valve regulator which opens when an additional gas is required by the patient, and closes when the additional gas is not required.

5. The isocapnia circuit of claim 1, wherein the valve includes a non-rebreathing valve through which gas exhaled from the patient is directed to a gas scavenger.

6. The isocapnia circuit of claim 1, wherein the source of fresh gas is operative to supply the fresh gas in an amount equal to minute ventilation of the subject minus ventilation of anatomic dead space of the subject.

7. The isocapnia circuit of claim 6, further comprising an anesthetic circuit selectively in communication with the exit port through the valve.

8. The isocapnia circuit of claim 7, further comprising a three-way stopcock to switch connection of the exit port to the isocapnia circuit or the anesthetic circuit.

9. The isocapnia circuit of claim 1, further comprising an inspiratory gas manifold in communication with the a side of the valve remote to the exit port, the inspiratory gas manifold comprising:
   a first port in communication with the source of fresh gas;
   a second port in communication with the gas reservoir;
   a third port in communication with the reserved gas supply; and
   a fourth port in communication with atmosphere.

10. The isocapnia circuit of claim 9, further comprising a self-inflating bag connected having one end in communication with the exit port through the valve and the other end connected to the inspiratory gas manifold.

11. The isocapnia circuit of claim 10, wherein the self-inflating bag comprises a one-way valve at the distal end for directing gas flowing therein.

12. The isocapnia circuit of claim 10, wherein the third port includes a one-way valve allowing reserved gas flowing into the inspiratory manifold.

13. The isocapnia circuit of claim 12, wherein the one-way valve of the third port is open when pressure in the insipratory manifold is about 5 cm $H_2O$ less than atmospheric pressure.

14. The isocapnia circuit of claim 10, wherein the fourth port includes a one-way valve allowing gas in the inspiratory gas manifold released to atmosphere.

15. The isocapnia circuit of claim 14, wherein the one-way valve of the fourth port opens when pressure in the inspiratory gas manifold is about 5 cm $H_2O$ greater than atmospheric pressure.

16. A non-rebreathing circuit for maintaining substantially constant isocapnia of a subject, the circuit comprising:
   a non-rebreathing valve preventing gas exhaled from the subject flowing into the circuit;
   a fresh gas source operative to supply a fresh gas containing physiologically insignificant amount of carbon dioxide to the subject through the non-rebreathing valve, wherein the fresh gas supplied to the subject is set with a rate equal to a baseline minute ventilation less a ventilation of anatomic dead space of the subject; and
   a reserved gas source operative to supply a reserved gas having a predetermined partial pressure of carbon dioxide to the subject through the non-rebreathing valve.

17. The non-rebreathing circuit of claim 16, wherein the predetermined partial pressure of carbon dioxide is equal to partial pressure of arterial blood of the subject.

18. The non-rebreathing circuit of claim 17, further comprising a gas reservoir operative to receive fresh gas in the circuit that is not breathed by the subject.

19. The non-rebreathing circuit of claim 16, wherein the reserved gas source is operative to supply the reserved gas only when minute ventilation of the subject exceeds the flow of the fresh gas supplied.

20. The non-rebreathing circuit of claim 16, wherein the fresh gas comprises oxygen.

21. The non-rebreathing circuit of claim 16, wherein the fresh gas comprises oxygen and nitrous oxide.

22. The non-rebreathing circuit of claim 16, wherein the reserved gas comprises carbon dioxide.

23. The non-rebreathing circuit of claim 16, wherein the non-rebreathing valve has a proximal end connected to the subject and a distal end in communication with either the fresh gas source or the reserved gas source according on level of minute ventilation of the subject.

* * * * *